United States Patent
Lee et al.

(10) Patent No.: US 7,129,275 B2
(45) Date of Patent: Oct. 31, 2006

(54) COMPOSITIONS FOR TREATING ACNE COMPRISING PHYTANDIOL AMINE

(75) Inventors: Jung-No Lee, Chungcheongnam-do (KR); Hyeong-Bae Kim, Cheonan-shi (KR); Jee-Hean Jeong, Suwon-shi (KR); Byong-Kee Jo, Anyang-shi (KR)

(73) Assignee: Coreana Cosmetics Co., Ltd., Cheonan-shi (KR)

( * ) Notice: Subject to any disclaimer, the term of this patent is extended or adjusted under 35 U.S.C. 154(b) by 149 days.

(21) Appl. No.: 10/494,337

(22) PCT Filed: Oct. 31, 2001

(86) PCT No.: PCT/KR01/01838

§ 371 (c)(1),
(2), (4) Date: Aug. 23, 2004

(87) PCT Pub. No.: WO03/037845

PCT Pub. Date: May 8, 2003

(65) Prior Publication Data

US 2004/0258720 A1      Dec. 23, 2004

(51) Int. Cl.
*A61K 31/13*   (2006.01)
*C07C 215/10*  (2006.01)

(52) U.S. Cl. ........................ 514/669; 564/507
(58) Field of Classification Search ................ 564/507
See application file for complete search history.

(56) References Cited

FOREIGN PATENT DOCUMENTS

EP          0 209 158       *  1/1987

\* cited by examiner

*Primary Examiner*—Brian Davis
(74) *Attorney, Agent, or Firm*—Nixon & Vanderhye P.C.

(57) ABSTRACT

The present invention relates to a phytandiol amine derivative represented by the following formula (I) and compositions for treating acne comprising the same:

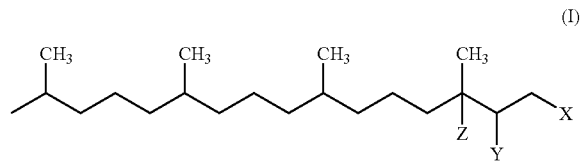

(I)

wherein each of Y and Z is OH with the proviso that X is $NH_2$, each of X and Z is zOH with the proviso that Y is $NH_2$, and each of X and Y is OH with the proviso that Z is $NH_2$.

4 Claims, No Drawings

COMPOSITIONS FOR TREATING ACNE COMPRISING PHYTANDIOL AMINE

This application is the US national phase of international application PCT/KR01/01838, filed 31 Oct. 2001, which designated the US.

BACKGROUND OF THE INVENTION

1. Field of the Invention

The present invention relates to novel phytandiol amine derivatives and their use for treatment or prevention of acne. More particularly, the present invention relates to novel phytandiol amine derivatives and compositions for improving or alleviating acne comprising the above derivatives as active ingredient.

2. Description of the Related Art

Acne is inflammatory disease or disorder generally developed at sebum gland in hair follicle of skin, of which etiopathology, although unclear, is suggested as follows: Excess secretion of sebum triggered by testosterone, one of androgenic hormones, contributes to dyskeratinization of pilosebaceous canal, and in turn results in blockage in orifice for secretion of sebum, thereby accumulation of sebum in hair follicle. Excess accumulation of sebum is responsible for overgrowth of acne-causing bacteria, e.g. *Propionibacterium acnes*, in such follicle, and the lipase secreted from the bacteria hydrolyzes the accumulated sebum to form free fatty acids giving rise to inflammation through irritation of skin. Also, acne-causing bacteria, recognized as antigen, elicit immune reaction of individuals, resulting in inflammatory reaction. In accordance with such mechanism, papule and inflammatory acne are developed, and when aggravated, wall of the follicle is disrupted and sequentially tissues are injured, finally leading to lesions of vesicular and pustule.

In an effort to inhibit generation and development of acne, a variety of pharmaceuticals formulated in the form of oral-administered drug or external preparation have been developed and employed. Such pharmaceuticals are: (a) anti-androgen agent for regulating secretion of androgenic hormones; (b) non-steroidal antiphlogostic agent exhibiting antinflammtory function; and (c) antimicrobial agents such as resorcinol, benzoyl peroxide, erythromycin and tetracycline to inhibit a growth of acne-causing bacteria. Recently, it is commonly employed to treat acne using retinoic acid and vitamin A derivatives.

Most of therapeutics for acne, however, is unfortunately suffered from adverse effects including inhibition of growth of epiderm, irritation or dyskeratinization of skin, resistance to antimicrobial agents and applicability.

Therefore, the use of low-irritating antimicrobial extracted from several plants has been recently attempted for controlling acne-causing bacteria in the field of cosmetics. Unfortunately, recent attempts as above-mentioned have recognized some drawbacks: (a) low antimicrobial activity and (b) inefficiency of separation and purification of active ingredient from natural sources.

Under such circumstances, many researches have continuously focused on substances or compositions for treating acne disease or disorder with both better compatibility to human body and greater efficacy.

U.S. Pat. No. 6,168,798 discloses non-irritating compositions for treating acne and other skin conditions comprising salicylic acid as active ingredient, and U.S. Pat. No. 6,174,892 discloses a method of treating acne with 5-alpha reductase inhibitors such as finasteride.

In addition, U.S. Pat. No. 4,775,663 suggests compositions for treating acne containing benzofuran derivatives and U.S. Pat. No. 5,019,567 discloses benzoyl peroxide-quaternary ammonium lipophilic salicylate based pharmaceutical and cosmetic compositions and their use especially in treatment of acne.

Throughout this application, various patents are reference and citations are provided in parentheses. The disclosure of these patents in their entities are hereby incorporated by references into this application in order to more fully describe this invention and the state of the art to which this invention pertains.

SUMMARY OF THE INVENTION

In one aspect of this invention, there is provided a phytandiol amine derivative represented by the following formula (I):

$$\text{(I)}$$

[Chemical structure: a chain with four $CH_3$ branches, ending in substituents X, Y, Z]

wherein each of Y and Z is OH with the proviso that X is $NH_2$, each of X and Z is OH with the proviso that Y is $NH_2$, and each of X and Y is OH with the proviso that Z is $NH_2$.

In another aspect of this invention, there is provided a cosmetic composition for improving or alleviating acne, which comprises: (a) a cosmetically effective amount of phytandiol amine derivatives as active ingredient represented by the following formula (I); and (b) a cosmetically acceptable carrier, $$\text{(I)}$$

[Chemical structure: a chain with four $CH_3$ branches, ending in substituents X, Y, Z]

wherein each of Y and Z is OH with the proviso that X is $NH_2$, each of X and Z is OH with the proviso that Y is $NH_2$, and each of X and Y is OH with the proviso that Z is $NH_2$.

In still another aspect of this invention, there is provided a pharmaceutical composition for treating or preventing acne, which comprises: (a) a pharmaceutically effective amount of phytandiol amine derivatives as active ingredient represented by the following formula (I); and
(b) a pharmaceutically acceptable carrier, $$\text{(I)}$$

[Chemical structure: a chain with four $CH_3$ branches, ending in substituents X, Y, Z]

wherein each of Y and Z is OH with the proviso that X is $NH_2$, each of X and Z is OH with the proviso that Y is $NH_2$, and each of X and Y is OH with the proviso that Z is $NH_2$.

Accordingly, it is an object of this invention to provide novel phytandiol amine derivatives.

It is another object of this invention to provide a cosmetic composition for improving or alleviating acne comprising the above derivatives as active ingredient.

It is still another object of this invention to provide a pharmaceutical composition for treating or preventing acne comprising the above derivatives as active ingredient.

Other objects and advantages of the present invention will become apparent from the detailed description to follow taken in conjugation with the appended claims.

DETAILED DESCRIPTION OF THIS INVENTION

The present invention is primarily directed to novel phytandiol amine derivatives. The derivatives have been prepared during the development of novel compounds highly effective in treating, alleviating or preventing certain skin disorders or diseases, generally called acne.

The phytandiol amine derivatives of this invention may be prepared from starting materials such as phytantriol and phytol, which is commercially available.

As known in formula (I), the phytandiol amine derivatives of this invention have amphiphilic property, thereby contributing to a good solubility in both aqueous solvent and non-aqueous solvent, as well as surface-activating property, and further exhibit high stability at high temperature, e.g., 90° C.–100° C., and at a very wide range of pH. The above-described properties are responsible for a high workability in the formulation of cosmetic or pharmaceutical composition, especially, composition for topical application.

The phytandiol amine derivatives of this invention may be classified into three classes. The terms, "phytandiol amine derivative (I)" or "phytandiol amine (I)", used herein, refer to a derivative of formula (I) in which each of Y and Z is OH with the proviso that X is $NH_2$. "Phytandiol amine derivative (II)" or "phytandiol amine (II)", as the terms are used herein, refer to a derivative of formula (I) in which each of X and Z is OH with the proviso that Y is $NH_2$. The terms, "phytandiol amine derivative (III)" or "phytandiol amine (III)", used herein, refer to a derivative of formula (I) in which each of X and Y is OH with the proviso that Z is $NH_2$.

In the compositions of the present invention, the compounds represented by formula (I) employed as active ingredient, are very useful for treating, alleviating and preventing acne, and exhibit an anti-acne efficacy through the inhibition of growth of acne-causing pathogens like *Propionibacterium acnes* and *Propionibacterium avidum*. The compounds of formula (I) show very low Minimum Inhibitory Concentration (hereinafter referred to as "MIC") against acne-causing pathogens.

The term "acne", used herein, to which the present compositions are applied, includes all skin diseases or disorders generally called acne as well as all skin diseases or disorders which have a similar pathology to one of acne. For examples, the acne includes, but not limited to, acne aggregate, bromide acne, common acne, congoblate acne, acne cosmetics, acne dtergicans, acne ephebica, acne fulminans, acne furunculoid, halogen acne, acne indurate, acne keloid, mechanical acne, acne medicamentosa, acne necrotica miliaris, acne neonatorum, acne oil, acne papulosa, pomade acne, premenstrual acne, acne rosacea, acne sycosiformis, tropical acne, acne venenata, and acne vulgaris.

In the compositions of this invention, the amount of phytadiol amine derivatives is preferably in the range of 0.001–50 wt %, more preferably, 0.01–20 wt % and the most preferably, 0.05–5 wt %.

The cosmetic compositions of this invention may be formulated in a wide variety of form, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray.

The cosmetically acceptable carrier contained in the present cosmetic composition, may be varied depending on the type of the formulation. For example, the formulation of ointment, pastes, creams or gels may comprise animal and vegetable fats, waxes, paraffins, starch, tragacanth, cellulose derivatives, polyethylene glycols, silicones, bentonites, silica, talc, zinc oxide or mixtures of these substances. In the formulation of powder or spray, it may comprise lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may comprise solvent, solubilizer and emulsifier, for example water, ethanol, isopropanol, ethyl carbonate, ethyl acetate, benzyl alcohol, benzyl benzoate, propylene glycol, 1,3-butylglycol, oils, in particular cottonseed oil, groundnut oil, maize germ oil, olive oil, castor oil and sesame seed oil, glycerol fatty esters, polyethylene glycol and fatty acid esters of sorbitan or mixtures of these substances. The formulation of suspension may comprise liquid diluents, for example water, ethanol or propylene glycol, suspending agents, for example ethoxylated isostearyl alcohols, polyoxyethylene sorbitol esters and poly oxyethylene sorbitan esters, micocrystalline cellulose, aluminum metahydroxide, bentonite, agar and tragacanth or mixtures of these substances.

The formulation of soap may comprise alkali metal salts of fatty acids, salts of fatty acid hemiesters, fatty acid protein hydrolyzates, isethionates, lanolin, fatty alcohol, vegetable oil, glycerol, sugars or mixtures of these substances.

Furthermore, the cosmetic compositions of this invention, may contain auxiliaries as well as carrier. The non-limiting examples of auxiliaries include preservatives, antioxidants, stabilizers, solubilizers, vitamins, colorants, odor improvers or mixtures of these substances In the pharmaceutical compositions of this invention, the pharmaceutically acceptable carrier may be conventional one for formulation, including lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxy benzoate, propylhydroxy benzoate, talc, stearic acid, magnesium and mineral oil, but not limited to. The pharmaceutical compositions of this invention, further may contain wetting agent, sweetening agent, emulsifying agent, suspending agent, preservatives, flavors, perfumes, lubricating agent, or mixtures of these substances.

The pharmaceutical compositions of this invention, may be administered orally or parenterally. The topical administration, especially topical application to skin, is the most preferable mode for the present compositions.

The correct dosage of the pharmaceutical compositions of this invention will vary according to the particular formulation, the mode of application, age, body weight and sex of the patient, diet, time of administration, condition of the patient, drug combinations, reaction sensitivities and severity of the disease. It is understood that the ordinary skilled physician will readily be able to determine and prescribe a correct dosage of this pharmaceutical compositions. An exemplary daily dosage unit for human host comprises an amount of from about 0.001 mg/kg to about 100 mg/kg.

According to the conventional techniques known to those skilled in the art, the pharmaceutical compositions of this invention can be formulated with pharmaceutical acceptable carrier and/or vehicle as described above, finally providing several forms including a unit dosage form. Non-limiting examples of the formulations include, but not limited to, a solution, a suspension or an emulsion, an extract, an elixir, a powder, a granule, a tablet, a capsule, emplastra, a liniment, a lotion and an ointment.

The compositions of this invention are significantly effective in treating, alleviating and preventing acne without irritation and keratinization of skin and induction of resistance to antimicrobial agents even the case of a long-term application.

The following specific examples are intended to be illustrative of the invention and should not be construed as limiting the scope of the invention as defined by appended claims.

EXAMPLE

Example I

Preparation of Phytandiol Amine Derivative [I]

In a reactor 0.3 g of phytantriol (0.91 mmol) was dissolved in 20 ml of normal hexane and stirred for 10 min. at a room temperature, followed by addition of 0.21 g (1.09 mmol) of para-toluene sulfonylchloride. Following the drop of the temperature of the reactor to 0° C., 0.11 g (1.09 mmol) of triethyl amine and a catalytic amount of pyridine were added dropwise and the temperature of the reactor was elevated to a room temperature, followed by stirring for 12 hr. Upon the completion of the reaction, the solvent was removed by distillation under reduced pressure. Then, 20 ml of chloroform was added to the concentrate for extraction and the extract was washed with saline. The washed extract was dried over anhydrous magnesium sulfate, followed by filtration and concentration to yield 0.48 g para-toluene sulfonyl phytandiol derivative as brown oil.

The yielded phytandiol derivative (0.48 g) was dissolved in 25 ml of dimethyl formamide and 0.06 g (1.00 mmol) of sodium azide was added, followed by reflux for 5 hr in order to substitute azide for para-toluene sulfonyl group. The reaction mixture was extracted with 50 ml of methylene chloride solution and washed with saline. Following drying over anhydrous magnesium sulfate, filtration and concentration, 0.29 g of azido phytandiol derivative was yielded.

In order to convert the azido phytandiol derivative to amine compound, 0.29 g of the yielded azido phytandiol (8.4 mmol) was subject to hydrogenation in ethyl alcohol with a catalytic amount of 10% palladium charcoal under 50 psi of hydrogen atmosphere for 3–4 hr, and finally 0.21 g of phytandiol amine derivative [I] (0.64 mmol) was obtained in the form of yellow gel in the overall yield of 70%: Anal. Calcd. for $C_{20}H_{43}NO_2$(329.33): C, 72,89; H, 13,15; N, 4,25; O, 9,71; Found C, 72,44; H, 13,51; N, 4,65; O, 9,98

Example II

Preparation of Phytandiol Amine Derivative [II]

In a reactor 0.3 g of phytol (1.0 mmol) was dissolved in 30 ml of methylene chloride and then the temperature of the reactor was decreased to 0° C. While maintaining the temperature of the reactor, to the mixture was added 0.45 g of 77% chloroperoxy benzoic acid. After the completion of the reaction, the resultant was extracted with 50 ml of chloroform to prepare phytol derivative epoxidated at 2- and 3-positions. The phytol derivative was reacted with ammonia gas for 5 hr. to produce 0.21 g of phytandiol amine derivative [II] in the yield of 64%: Anal. Calcd. for $C_{20}H_{43}NO_2$(329.33): C, 72,89; H, 13,15; N, 4,25; O, 9,71; Found C, 72,44; H, 13,51; N, 4,65; O, 9.98

Example III

Preparation of Phytandiol Amine Derivative [III]

One g of phytantriol (3.0 mmol) was refluxed using deanstock apparatus for 15 hr in 25 ml of acetone solution with toluene sulfonic acid as catalyst. After the completion of the reaction, the acetone solvent was removed under reduced pressure and the resultant was extracted with chloroform solution. The extract was washed with saturated sodium bicarbonate solution and was again washed with saline to obtain 0.3 g of (2-(2,2-dimethyl-[1,3]dioxolan-4-yl)-6,10,14-trimethyl-pentadecan-2-ol) of which 1- and 2-positions were protected, which is represented by the following formula (IV):

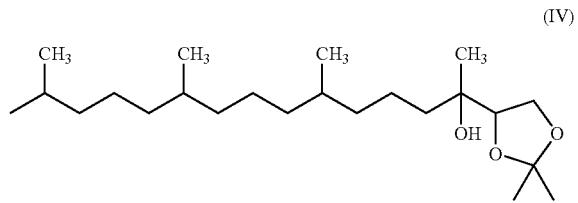

Thereafter, in 20 ml of normal hexane was dissolved 0.3 g of (2-(2,2-dimethyl-[1,3]dioxolan-4-yl)-6,10,14-trimethyl-pentadecan-2-ol), and stirred for 10 min. at a room temperature, followed by addition of 0.18 g (0.97 mmol) of para-toluene sulfonylchloride. After the drop of the temperature of the reactor to 0° C., 3 equivalents of pyridine were added and the temperature of the reactor was elevated to a room temperature, followed by stirring for 12 hr. Upon the completion of the reaction, the solvent was removed by distillation under reduced pressure. Then, 20 ml of chloroform was added to the concentrate for extraction and the extract was washed with saline. The washed extract was dried over anhydrous magnesium sulfate, followed by filtration and concentration to yield 0.41 g of a compound substituted at 3-position with toluene sulfonyl in the form of yellow oil. In 20 ml of 2N HCl was dissolved 0.41 g of the yellow oil, and then was reacted for 6 hr at 80° C. to yield 0.21 g of 1,2-phytandiol derivative of which ring structure is cleaved.

The phytandiol derivative yielded (0.21 g) was dissolved in 25 ml of dimethyl formamide and 0.06 g (1.00 mmol) of sodium azide was added, followed by reflux for 5 hr to produce 0.15 g of phytandiol derivative substituted with azide. In order to reduce the azide-substituted phytandiol derivative to amine compound, 0.15 g of the azido phytandiol yielded was subject to hydrogenation in ethyl alcohol with a catalytic amount of 10% palladium charcoal under 50 psi of hydrogen atmosphere for 3–4 hr, and finally 0.20 g of phytandiol amine derivative [III] was obtained in the yield of 50%: Anal. Calcd. for $C_{20}H_{43}NO_2$(329.33): C, 72,89; H, 13,15; N, 4,25; O, 9,71; Found C, 72,51; H, 13,04; N, 4,54; O, 9,43

Example IV

Evaluation on Minimum Inhibitory Concentration

To evaluate an antimicrobial activity of the phytandiol amine of this invention against acne pathogen, the minimum inhibitory concentration (hereinafter referred to as "MIC") of the samples shown in Table 1 was measured as follows:

The sample to be tested was added to reinforced clostridial agar medium (available from Difco Co.) in the amount of 0.001–0.1%, followed by solidification of the medium. The suspension of acne pathogenic bacteria found in Table 1 was streaked on the surface of the medium and the medium was incubated for 3 days at 35° C. under anaerobic condition. The MIC was measured by the determination of the minimum concentration to completely inhibit the growth of the acne pathogenic bacteria, of which results are indicated in Table 1.

TABLE 1

| Sample/Pathogen | P. acnes ATCC 6919 | P. acne ATCC 11828 | P. avidum ATCC 25577 |
|---|---|---|---|
| Phytandiol amine [I] | 0.002 | 0.002 | 0.002 |
| Phytandiol amine [II] | 0.002 | 0.002 | 0.002 |
| Phytandiol amine [III] | 0.003 | 0.004 | 0.003 |
| Tea tree oil | 1.0 | 0.2 | 1.0 |
| Erythromycin | 0.02 | 0.02 | 0.02 |
| Chitosan | 0.2 | 0.2 | 0.2 |
| Benzoyl peroxide | 0.1 | 0.1 | 0.1 |

As demonstrated in Table 1, the phytandiol amine derivatives of this invention represent antimicrobial activity against acne pathogens 10–50 times greater than erythromycin and benzoyl peroxide which are conventionally used as a therapeutic agent for acne.

Furthermore, the phytandiol amine derivatives of this invention are improved in terms of workability and skin-compatibility, thereby leading to little adverse effects. Therefore, the phytandiol amine derivatives of this invention can be excellent agents for treating acne and the compositions comprising the same are also expected to exhibit a remarkable treatment effect to acne.

Example V

Evaluation on Antimicrobial Activity Against Acne Pathogen of the Formulation Comprising the Present Compounds To elucidate antimicrobial activity against acne pathogens of the compositions comprising the phytandiol amine derivatives of this invention, a particular formulation of skin lotion as external application was prepared as the following Table 2. In Table 2, the amount of constituents is expressed in terms of wt %.

TABLE 2

| Ingredients | Prep. 1 | Prep. 2 | Comp. Exam. |
|---|---|---|---|
| Phytandiol amine [I] | 0.05 | 0.1 | — |
| Glycerine | 5.0 | 5.0 | 5.0 |
| 1,3-butylene glycol | 3.0 | 3.0 | 3.0 |
| PEG-1500 | 1.0 | 1.0 | 1.0 |
| DL-panthenol | 0.3 | 0.3 | 0.3 |
| EDTA | 0.02 | 0.02 | 0.02 |
| Benzophenone-9 | 0.04 | 0.04 | 0.04 |
| Sodium hyaluronate | 5.0 | 5.0 | 5.0 |
| Ethanol | 10.0 | 10.0 | 10.0 |
| Octyldodeces-16 | 0.2 | 0.2 | 0.2 |
| Polysorbate 20 | 0.2 | 0.2 | 0.2 |
| Allantoin | 0.1 | 0.1 | 0.1 |
| Preservative, perfume, colorant | Minute amount | minute amount | minute amount |
| Distilled water | Residual | Residual | residual |
| Total | 100 | 100 | 100 |

The antimicrobial activities against acne-causing bacteria of the skin lotions of preparative examples 1 and 2, and comparative example were measured as follows: The acne-causing bacteria were cultured at 35° C. under anaerobic condition, the colonies formed were taken with a platinum loop and were appropriately diluted by suspending in phosphate-buffered saline. 10 ml of reinforced clostridial agar medium were poured into each of plates and solidified, and then the diluted solution containing acne-causing bacteria was inoculated into each of the plates to the extent of 300–500 cfu. The plates were cultured in an anaerobic incubator and the number of colonies formed was counted, which is considered as the number of the original acne-causing bacteria ($N_{ori}$).

The skin lotions of preparative examples 1 and 2, and comparative example were respectively mixed with reinforced clostridial agar medium to the extent of 10%, the acne-causing bacteria was inoculated into the mixture and cultured as above. The number of colonies formed is considered as the number of the final acne-causing bacteria ($N_{fin}$). The antimicrobial activity against acne-causing bacteria was calculated in accordance with following equation, which is indicated in Table 3.

Equation $$\text{Antimicrobial Activity}(\%)=[(N_{ori}-N_{fin})/N_{ori}]\times 100$$

More than 90% of antimicrobial activity is evaluated as the possession of antimicrobial activity against acne-causing bacteria.

TABLE 3

| Items | Prep. 1 | Prep. 2 | Comp. Exam. |
|---|---|---|---|
| No. of original acne-causing bacteria ($N_{ori}$) | 510 | 475 | 380 |
| No. of final acne-causing bacteria ($N_{fin}$) | 31 | 2 | 219 |
| Antimicrobial activity against acne-causing bacteria (%) | 93.9 | 99.5 | 42.3 |
| Evaluation | adequate | adequate | inadequate |

As found in Table 3, the formulations comprising the phytandiol amine derivative [I] of this invention exhibit antimicrobial activity against acne-causing bacteria much greater than the formulation without the derivative. In particular, the formulation containing 0.1 wt % of phytandiol amine derivative [I] approaches to 100% of antimicrobial activity.

While not shown in this specification, the formulations containing the phytandiol amine derivatives [II] or [III] of this invention give almost the same antimicrobial activity as one containing the phytandiol amine derivative [I]

Consequently, it is sure that the compositions comprising the phytandiol amine derivatives of this invention are highly effective in treating or preventing acne.

Example VI

Evaluation on Improving or Alleviating Acne

First, 60 women aged 17–29 years, who had acne symptom on their face, were randomly divided to three groups. The formulations of preparative examples 1 or 2, or comparative example were topically applied twice a day to three groups, respectively, for six weeks, in the morning and evening. The improving or alleviating effect for acne was assessed with the opinion from the tested women, which is indicated in Table 4.

TABLE 4

| Time Period | Prep. 1 | Prep. 2 | Com. Exam. |
| --- | --- | --- | --- |
| 1 week | ± | ± | ± |
| 2 weeks | + | + | ± |
| 3 weeks | + | ++ | ± |
| 4 weeks | ++ | +++ | ± |
| 5 weeks | +++ | +++ | ± |
| 6 weeks | +++ | +++ | ± |

Note.
+++: showing excellent improvement efficacy
++: showing significant improvement efficacy
+: showing slight improvement efficacy
±: not showing improvement efficacy but not showing aggravation efficacy
−: showing aggravation efficacy As demonstrated in Table 4, the formulations of skin lotion containing phytandiol amine derivative [I] of this invention exhibit excellent improvement or alleviation effect on acne symptom, which appears explicitly from about 3 weeks after application. Furthermore, the composition of this invention did not lead to irritation of skin, erythema and itch.

Formulation Example

The following exemplified compositions were formulated according to conventional methods, which comprise the phytandiol amine [I] of this invention as active ingredient while the formulated compositions can be also applied to other phytandiol amine derivatives of this invention. Therefore, those skilled in the art will promptly recognize appropriate variations from the formulations both as to ingredients and as to the amount thereof.

Formulation I

Formulation I comprising the phytandiol amine [I] was prepared in the form of astringent cosmetic liquid, of which composition is found in Table 5.

TABLE 5

| Ingredients | Amount (wt %) |
| --- | --- |
| Phytandiol amine [I] | 0.1 |
| Glycerine | 2.0 |
| 1,3-butylene glycol | 2.0 |

TABLE 5-continued

| Ingredients | Amount (wt %) |
| --- | --- |
| Allantoin | 0.2 |
| DL-panthenol | 0.2 |
| EDTA | 0.02 |
| Benzophenone-9 | 0.04 |
| Sodium hyaluronate | 3.0 |
| Ethanol | 15.0 |
| Polysorbate 20 | 0.3 |
| Preservative, perfume, colorant | Minute quantity |
| Distilled water | Residual quantity |

Formulation II

Formulation II comprising the phytandiol amine [I] was prepared in the form of nutrient cosmetic liquid, of which composition is found in Table 6.

TABLE 6

| Ingredients | Amount (wt %) |
| --- | --- |
| Phytandiol amine [I] | 0.1 |
| Glyceryl stearate | 1.5 |
| Stearyl alcohol | 1.5 |
| Lanoline | 1.5 |
| Polysorbate | 1.3 |
| Hardened plant oil | 1.0 |
| Mineral oil | 5.0 |
| Squalane | 3.0 |
| Trioctanoine | 2.0 |
| Dimethicone | 0.8 |
| Tocopheryl acetate | 0.5 |
| Carboxyvinyl polymer | 0.12 |
| Glycerine | 5.0 |
| 1,3-butylene glycol | 3.0 |
| Sodium hyaluronate | 5.0 |
| Triethanol amine | 0.12 |
| preservative, perfume, colorant | Minute quantity |
| Distilled water | Residual quantity |

Formulation III

Formulation III comprising the phytandiol amine [I] was prepared in the form of nutrient cream, of which composition is found in Table 7.

TABLE 7

| Ingredients | Amount (wt %) |
| --- | --- |
| Phytandiol amine [I] | 0.1 |
| Lipophilic monostearyl glycerine | 2.0 |
| Stearyl alcohol | 2.2 |
| Stearic acid | 1.5 |
| Wax | 1.0 |
| Polysorbate 60 | 1.5 |
| Sorbitan stearate | 0.6 |
| Hardened plant oil | 1.0 |
| Squalane | 3.0 |
| Mineral oil | 5.0 |
| Trioctanoine | 5.0 |
| Dimethicone | 1.0 |
| Sodium magnesium silicate | 0.1 |
| Glycerine | 5.0 |
| Betaine | 3.0 |
| Triethanol amine | 1.0 |
| Sodium hyaluronate | 4.0 |
| Preservative, perfume, colorant | Minute quantity |
| Distilled water | Residual quantity |

Formulation IV

Formulation IV comprising the phytandiol amine [I] was prepared in the form of massage cream, of which composition is found in Table 8.

TABLE 8

| Ingredients | Amount (wt %) |
| --- | --- |
| Phytandiol amine [I] | 0.1 |
| Lipophilic monostearyl glycerine | 1.5 |
| Stearyl alcohol | 1.5 |
| Stearic acid | 1.0 |
| Polysorbate 60 | 1.5 |
| Sorbitan stearate | 0.6 |
| Isostearylisostearate | 5.0 |
| Squalane | 5.0 |
| Mineral oil | 35.0 |
| Dimethicone | 0.5 |
| Hydroxyethyl cellulose | 0.12 |
| Glycerine | 6.0 |
| Triethanol amine | 0.7 |
| Preservative, perfume, colorant | Minute amount |
| Distilled water | Residual amount |

Formulation V

Formulation V comprising the phytandiol amine [I] was prepared in the form of essence, of which composition is found in Table 9.

TABLE 9

| Ingredients | Amount (wt %) |
| --- | --- |
| Phytandiol amine [I] | 0.1 |
| Glycerine | 10.0 |
| Betaine | 5.0 |
| PEG-1500 | 2.0 |
| Allantoin | 0.1 |
| DL-panthenol | 0.3 |
| EDTA | 0.02 |
| Benzophenone-9 | 0.04 |
| Hydroxyethylcellulose | 0.1 |
| Sodium hyaluronate | 8.0 |
| Carboxyvinyl polymer | 0.2 |
| Triethanol amine | 0.18 |
| Octyldodeces-16 | 0.4 |
| Octyldodecanol | 0.3 |
| Ethanol | 6.0 |
| preservative, perfume, colorant | Minute amount |
| Distilled water | Residual amount |

Formulation VI

Formulation VI comprising the phytandiol amine [I] was prepared in the form of facial pack, of which composition is found in Table 10.

TABLE 10

| Ingredients | Amount (wt %) |
| --- | --- |
| Phytandiol amine [I] | 1.0 |
| Polyvinyl alcohol | 15.0 |
| Cellulose gum | 0.15 |
| Glycerine | 3.0 |
| PEG-1500 | 2.0 |
| Cyclodextrine | 0.15 |
| DL-panthenol | 0.4 |
| Allantoin | 0.1 |
| Glyceryl ammonium | 0.3 |
| Nicotine amide | 0.5 |
| Ethanol | 6.0 |

TABLE 10-continued

| Ingredients | Amount (wt %) |
| --- | --- |
| PEG-40 hardened castor oil | 0.3 |
| Preservative, perfume, colorant | Minute amount |
| Distilled water | Residual amount |

Formulation VII

Formulation VII comprising the phytandiol amine [I] was prepared in the form of soap, of which composition is found in Table 11.

TABLE 11

| Ingredients | Amount (wt %) |
| --- | --- |
| Palm oil fatty acid | 1.5 |
| Titania | 0.5 |
| Glycerine | 0.5 |
| EDTA-2Na | 0.15 |
| Perfume | 0.7 |
| Phytandiol amine [I] | 0.5 |
| Colorant | Adequate quantity |
| Soap chip base (water content, 15 wt %) | To 100 |

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A cosmetic composition for improving or alleviating acne, which comprises:
   (a) a cosmetically effective amount of phytandiol amine derivative as active ingredient represented by the following formula (I); and
   (b) a cosmetically acceptable carrier,

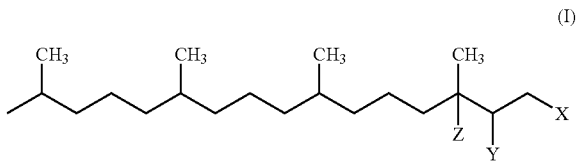

wherein each of Y and Z is OH with the proviso that X is $NH_2$, each of X and Z is OH with the proviso that Y is $NH_2$, and each of X and Y is OH with the proviso that Z is $NH_2$.

2. The composition according to claim 1, wherein the acne is selected from the group consisting of acne aggregata, bromide acne, common acne, congoblate acne, acne cosmetica, acne dtergicans, acne ephebica, acne fulminans, acne furunculoid, halogen acne, acne indurate, acne keloid, mechanical acne, acne medicamentosa, acne necrotica miliaris, acne neonatorum, acne oil, acne papulosa, pomade acne, premenstrual acne, acne rosacea, acne sycosiformis, tropical acne, acne venenata and acne vulgaris.

3. The composition according to claim 1, wherein the phytandiol amine derivative is present in an amount of 0.01–20 wt % based on the total weight of the composition.

4. The composition according to claim 1, wherein the cosmetic composition is in the form of one selected from the group consisting of a solution, a suspension, an emulsion, a paste, an ointment, a gel, a cream, a lotion, a powder, a soap, a surfactant-containing cleanser, an oil, a powder foundation, an emulsion foundation, a wax foundation and a spray.

* * * * *